United States Patent [19]

Volkamer et al.

[11] Patent Number: 4,553,984
[45] Date of Patent: * Nov. 19, 1985

[54] REMOVAL OF $CO_2$ AND/OR $H_2S$ FROM GASES

[75] Inventors: Klaus Volkamer, Frankenthal; Eckhart Wagner, Ludwigshafen; Ulrich Wagner, Limburgerhof, all of Fed. Rep. of Germany

[73] Assignee: BASF Aktiengesellschaft, Fed. Rep. of Germany

[*] Notice: The portion of the term of this patent subsequent to Nov. 5, 2002 has been disclaimed.

[21] Appl. No.: 586,720

[22] Filed: Mar. 6, 1984

[51] Int. Cl.⁴ .............................................. B01D 47/00
[52] U.S. Cl. ........................................... 55/46; 55/55; 55/68; 55/73; 423/228
[58] Field of Search ............... 55/38, 40, 46, 48, 51, 55/68, 73, 55; 423/228, 229

[56] References Cited

U.S. PATENT DOCUMENTS

| | | | |
|---|---|---|---|
| 4,035,166 | 7/1977 | van Hecke | 55/38 |
| 4,080,424 | 3/1978 | Miller et al. | 55/73 X |
| 4,100,257 | 7/1978 | Sartori et al. | 55/73 X |
| 4,330,305 | 5/1982 | Kusessner et al. | 55/48 |
| 4,452,763 | 6/1984 | van de Kaats et al. | 423/228 |

OTHER PUBLICATIONS

A. L. Kohl-F. C. Riesenfeld, Gas Purification, 3rd Edition, 1979.

Primary Examiner—Charles Hart
Attorney, Agent, or Firm—Keil & Weinkauf

[57] ABSTRACT

$CO_2$ and/or $H_2S$ are removed from gases which contain $CO_2$ and/or $H_2S$ by a process in which the said gas is treated, in an absorption stage at from 40° to 100° C., with an aqueous absorption liquid containing from 20 to 70% by weight of methyldiethanolamine, the treated gas is taken off at the top of the absorption stage, the aqueous absorption liquid laden with $CO_2$ and/or $H_2S$ is taken off at the bottom of the absorption stage and then regenerated by being let down in one or more flash stages, the flash gases being taken off at the top of the flash stage or flash stages, the losses of water as a result of water present in the gas streams taken off at the top of the absorption stage and of the flash stage or flash stages are compensated by feeding in, at the bottom of the last flash stage or, where only one flash stage is used, at the bottom of this, and amount of steam corresponding to the water loss, and the regenerated absorption liquid is recycled to the absorption stage.

1 Claim, 1 Drawing Figure

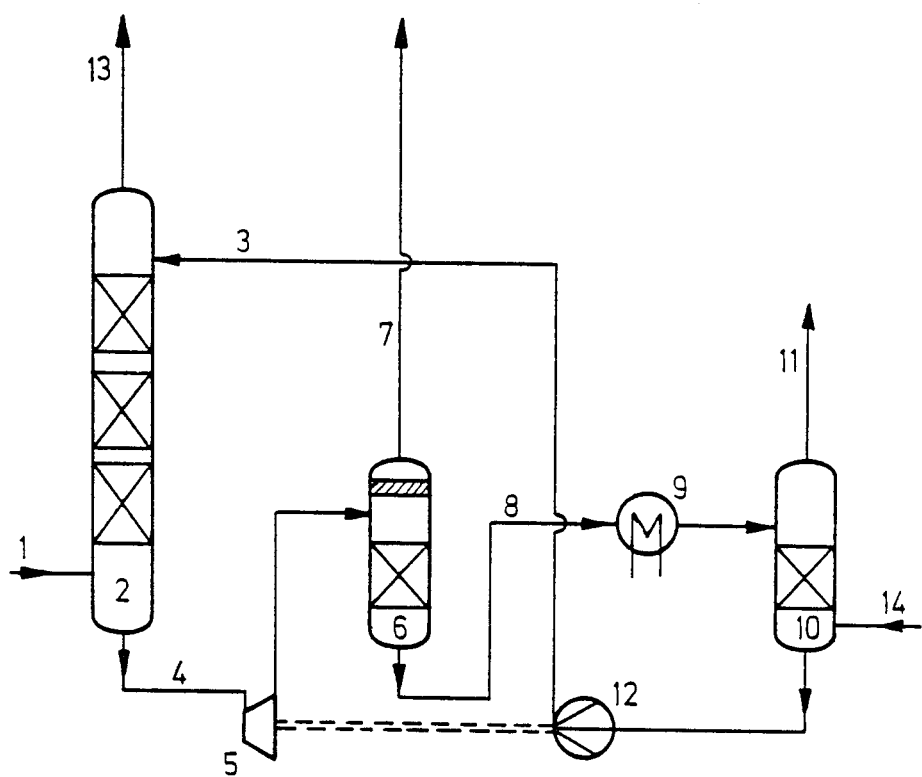

REMOVAL OF CO₂ AND/OR H₂S FROM GASES

The present invention relates to a process for the removal of $CO_2$ and/or $H_2S$ from gases by means of an aqueous absorption liquid.

It has been disclosed, for example in A. L. Kohl—F. C. Riesenfeld, Gas Purification, 3rd Edition, 1979, that aqueous solutions of monoethanolamine or diethanolamine or a mixture of cyclotetramethylenesulfone and an aqueous solution of diisopropanolamine can be used as solvents for removing $CO_2$ and/or $H_2S$ from gases. In these processes, it is necessary for the solvent which is laden with $CO_2$ and, where relevant, $H_2S$ to be regenerated in a stripping column by feeding in steam; this requires a substantial amount of energy. Where $CO_2$ and, where relevant/$H_2S$ are removed from natural gases containing higher hydrocarbons by means of a mixture of cyclotetramethylenesulfone and an aqueous solution of diisopropanolamine, an additional disadvantage is that the higher hydrocarbons have a relatively high solubility in this solvent, so that the acid gas taken off at the top of the stripping column has a relatively high hydrocarbon content which, if the acid gas contains $H_2S$, can lead to difficulties in a downstream Claus unit. Furthermore, primary or secondary alkanolamines, eg. monoethanolamine or diethanolamine, can only be used in the form of relatively dilute aqueous solutions since higher concentrations can cause severe damage to plant components as a result of corrosion.

There has therefore been a need for a process for removing $CO_2$ and/or $H_2S$ from gases, by means of which the disadvantages of the conventional prpcesses can be avoided.

It is an object of the present invention to provide a process for removing $CO_2$ and/or $H_2S$ from gases which contain $CO_2$ and/or $H_2S$, which requires a small amount of energy for its operation and in which the loss of higher hydrocarbons can be kept low.

We have found that this and other objects and advantages are achieved, in accordance with this invention, by a process for removing $CO_2$ and/or $H_2S$ from gases which contain $CO_2$ and/or $H_2S$, wherein the said gas is treated, in an absorption stage at from 40° to 100° C., with an aqueous absorption liquid containing from 20 to 70% by weight of methyldiethanolamine, the treated gas is taken off at the top of the absorption stage, the aqueous absorption liquid laden with $CO_2$ and/or $H_2S$ is taken off at the bottom of the absorption stage and then regenerated by being let down in one or more flash stages, the flash gases being taken off at the top of the flash stage or flash stages, the losses of water as a result of water present in the gas streams taken off at the top of the absorption stage and of the flash stage or flash stages are compensated by feeding in, at the bottom of the last flash stage or, where only one flash stage is used, at the bottom of this, an amount of steam corresponding to the water loss, and the regenerated absorption liquid is recycled to the absorption stage.

In the novel process, the solvent laden with $CO_2$ and/or $H_2S$ is regenerated without the use of a stripping column, simply by flashing in one or more flash stages, so that both capital costs and energy costs can be substantially reduced. Furthermore, in the novel process it is possible to use relatively high methyldiethanolamine concentrations in the absorption liquid without this entailing corrosion damage in the gas wash unit. Another advantage of the process is that water losses which arise in gas wash units as a result of water being present in the gas streams taken off at the top of the absorption column and of the flash chambers are compensated by feeding in, at the bottom of the final flash stage, an amount of steam corresponding to the water loss. By means of this procedure, the water balance of the gas wash unit as well as its heat balance can be regulated, so that the heat exchanger provided for regulating the heat balance in the gas wash unit can be reduced in size or, if appropriate, completely dispensed with.

Examples of gases which can be treated using the novel process are coal gasification gases, synthesis gases, coke oven gases and, preferably, natural gases. The process is advantageously used for removing $CO_2$ and/or $H_2S$ from natural gases which contain higher hydrocarbons in addition to methane. These higher hydrocarbons are in general $C_2$-$C_{30}$-hydrocarbons, preferably $C_2$-$C_{20}$-hydrocarbons, in particular $C_2$-$C_{12}$-hydrocarbons, which as a rule are aliphatic, eg. ethane, propane, isobutane, n-butane, isopentane, n-pentane, the hexanes, heptanes, octanes, nonanes and decanes and the higher homologs. The higher hydrocarbons can contain, in addition to aliphatic hydrocarbons, aromatic hydrocarbons such as benzene. In general, the natural gases contain from 0.1 to 40, preferably from 0.5 to 30, in particular from 1 to 20, mole % of the higher hydrocarbons.

The gases contain in general from 1 to 90, preferably from 2 to 90, in particular from 5 to 60, mole % of $CO_2$. They can also contain $H_2S$ as a further acid gas, or can contain $H_2S$ alone, for example in an amount of from a few mole ppm, for example 1 mole ppm, to 50 mole %.

The solvent used for the novel process is an aqueous absorption liquid containing from 20 to 70, preferably from 30 to 65, in particular from 40 to 60, % by weight of methyldiethanolamine. Advantageously, an aqueous methyldiethanolamine solution is employed, for example an aqueous solution of technical-grade methyldiethanolamine. In an advantageous embodiment of the process, the aqueous methyldiethanolamine solution used additionally contains from 0.1 to 1, preferably from 0.2 to 0.8, in particular from 0.25 to 0.6, mole/liter of a secondary amine or alkanolamine, preferably methylmonoethanolamine, very particularly advantageously piperazine. The novel process is carried out as follows: the gas containing $CO_2$ and/or $H_2S$ is first treated, in an absorption stage, with the methyldiethanolamine-containing absorption liquid at from 40 to 100° C., preferably from 50 to 90° C., in particular from 60 to 80° C. The pressure in the absorption stage is in general from 10 to 110, preferably from 20 to 100, in particular from 30 to 90, bar. The absorption stage is advantageously an absorption column, in general a packed column or a column equipped with trays. Advantageously, the has to be treated is fed in at the bottom and the absorption liquid is fed in at the top of the absorption column, the acid gases $CO_2$ and/or $H_2S$ being washed out by a countercurrent procedure. While any $H_2S$ present is advantageously washed out to a substantial extent, in general so that the treated gas has an $H_2S$ content of not more than 120, preferably not more than 10, in particular not more than 3, mole ppm, it may be advantageous to wash out the $CO_2$ from the gas so that the treated gas contains not more than about 0.5–6, preferably from 0.5 to 5, in particular from 1 to 4, mole % of $CO_2$. The treated gas is advantageously taken off at the top of the absorption stage, expediently at a point above the feed. of the absorption liquid. The absorption liquid laden with the acid gases $CO_2$ and/or $H_2S$ is advantageously taken off at the bottom of the absorption zone.

The laden absorption liquid is then regenerated in one or more flash stages. In the last flash stage, or in the single flash stage where only one such stage is employed, the pressure is advantageously let down to about 1-3, preferably from 1 to 1.8, in particular from 1 to 1.5, bar. It may also be advantageous to operate the last flash stage or the single flash stage under reduced pressure, for example under from 0.5 to about 1, preferably from 0.8 to about 1, bar. It can be advantageous to use two or more, for example from 2 to 5, preferably 2 or 3, in particular 2, flash stages for the regeneration of the laden absorption liquid. Preferably, the pressure of the latter is let down to not less than 5 bar in the first flash stage after the absorption stage. It can be advantageous if the pressure to which the absorption liquid is let down in this first flash stage is furthermore not less than the partial pressure of $CO_2$ or of $H_2S$, or of the sum of the partial pressures of $CO_2$ and $H_2S$, in the gas fed into the absorption stage and containing $CO_2$ and/or $H_2S$. In this procedure, the evaporation of water and the associated energy losses as well as the losses of hydrocarbons can be kept particularly low. Flashing is advantageously carried out using flash chambers which can, for example, also be in the form of columns. These flash chambers need not contain special baffles. However, it is also possible to use columns equipped with baffles, eg. packed columns.

As a rule, heat is supplied to the process to compensate for heat losses due to the process, for example those resulting from the flash. This is advantageously done in a heat exchange zone which is located upstream from the last flash stage, or from the single flash stage where only one such stage is used, and in which the laden absorption liquid is heated before flashing in the last or single flash stage. As a rule, the absorption liquid is heated by not more than 20° C. in the exchange zone, reaching a temperature of in general not more than 90° C., as a rule not more than 85° C. In general heat exchangers, eg. a tubular heat exchanger, are used for the heat exchange zone.

To compensate for water losses which arise in the process as a result of the presence of water in the gas streams taken off at the top of the absorption stage and of the flash stage or flash stages, an amount of steam corresponding to the water loss is fed in at the bottom of the final flash stage or, where only one flash stage is used, at the bottom of this single flash stage. As a rule, the water present in the gas streams taken off is essentially removed in the form of steam. Low-pressure, medium-pressure or high-pressure steam, eg. steam under 1-100 bar, can be fed to the bottom of the flash stage. Preferably, low-pressure steam, eg. steam under 1.5 to 10, advantageously from 1.5 to 5, bar, is used, since this steam is in general cheaply available. The feed, according to the invention, of steam to the flash stage permits control of the water balance as well as of the heat balance of the gas wash unit. Accordingly, in a preferred embodiment of the process, in order to compensate for process-dependent heat losses the process is either supplied with heat both in the heat exchanger zone upstream from the final flash stage or, where only one flash stage is used, upstream from this single flash stage, and by means of the steam fed in at the bottom of the final flash stage or of the single flash stage, or supplied with heat solely by the latter method.

The acid gases $CO_2$ and/or $H_2S$ are advantageously taken off at the top of the last flash stage. Where the acid gas removed contains $H_2S$, it is advantageously worked up by oxidizing the $H_2S$, for example in a Claus unit. The regenerated absorption liquid taken off at the bottom of the last flash stage is recycled to the absorption zone.

The example which follows illustrates the invention in more detail, the course of the process being shown diagrammatically in the FIGURE.

A gas which contains $CO_2$ and/or $H_2S$, for example a natural gas containing higher hydrocarbons, eg. aliphatic $C_2$–$C_{10}$-hydrocarbons, is passed under superatmospheric pressure, via line 1, into the bottom of absorption column 2. At the same time, an absorption liquid comprising from 20 to 70% strength by weight aqueous methyldiethanolamine solution is passed via line 3 to the top of the absorption column. The absorption liquid, which is fed counter-current to the gas, becomes laden with the acid gases $CO_2$ and/or $H_2S$, and the laden absorption liquid is taken off at the bottom of the absorption column via line 4. The washed gas is taken off at the top of the absorption column via line 13. The stream of laden absorption liquid 4 is then let down, advantageously to not less than 5 bar, in a flash chamber 6, for example via a valve or, preferably, an expansion turbine 5. In this stage, an intermediate flash gas containing hydrocarbons and $CO_2$ is liberated from the absorption liquid and is taken off at the top of flash chamber 6 via line 7. At the bottom of flash chamber 6, the absorption liquid which has been partially let down is taken off via line 8 and heated in heat exchanger 9, for example by from 1° to 15° C., and the heated absorption liquid is let down, for example to 1-2 bar, in a second flash chamber 10. This liberates a $CO_2$-rich flash gas, for example having a $CO_2$ concentration of 98 mole %, and this gas is taken off at the top of flash chamber 10 via line 11. To compensate for water losses of the system, steam, eg. low-pressure steam under 2.5 bar, is passed into the bottom of flash chamber 10 via line 14. The regenerated absorption liquid taken off at the bottom of flash chamber 10 is recycled to the top of absorption column 2 with the aid of a circulatory pump 12.

The Example which follows illustrates the invention.

EXAMPLE

In an absorption column, 3.15 kmol hour of a $CO_2$-containing natural gas are washed, under 75 bar, with a 50% strength by weight aqueous methyldiethanolamine solution as the absorption liquid. The gas to be treated has the following composition:
$CO_2$—10.0 mole %
$CH_4$—75.0 mole %
higher hydrocarbons
($C_2$–$C_{12}$-hydrocarbons—15.0 mole %.

The temperature of the absorption liquid in the feed to the absorption column is 70° C. The $CO_2$ content in the washed gas is 2.0 mole %. The laden washing agent which leaves the absorption column is let down to 20 bar in a first flash chamber. In this procedure, 0.04 kmol/liter of a hydrocarbon-rich intermediate flash gas having a $CO_2$ concentration of 34.3 mole % is liberated from the solution and is taken off at the top of the first flash chamber. The partially let down absorption liquid is then heated in a heat exchanger. The heated absorption liquid is let down to 1.3 bar in a second flash chamber. In this procedure 0.241 kmol/hour of a $CO_2$-rich flash gas having a $CO_2$ concentration of 97.55 mole %, a methane concentration of 1.68 mole % and a concentration of higher hydrocarbons of 0.77 mole % is liberated and is taken off at the top of the second flash chamber. To compensate for the Water losses of the system, low-pressure steam under 2.5 bar is passed into the bottom of the second flash chamber. The absorption liquid taken off at the bottom of the flash chamber is recycled to the top of the absorption column with the aid of a circulatory pump.

We claim:

1. A process for removing $CO_2$ and/or $H_2S$ from a gas containing $CO_2$ and/or $H_2S$, which comprises:

(a) treating said gas in an absorption stage at from 40° to 100°C. and at a pressure of from 10 to 110 bar with an aqueous absorption liquid containing from 20 to 70% by weight of methyldiethanolamine by feeding in the gas at the bottom and the aqueous absorption liquid at the top of the absorption stage, $CO_2$ and/or $H_2S$ being washed out by a counter-current procedure;

(b) taking off the treated gas at the top of the absorption stage;

(c) taking off the aqueous absorption liquid laden with $CO_2$ and/or $H_2S$ at the bottom of the absorption stage;

(d) regenerating the laden aqueous absorption liquid by flashing it in one or more flash stages, operating the last stage, or the single flash stage where only one such stage is employed, under a pressure of from about 1 to 3 bar or under reduced pressure, the flash gases being taken off at the top of the flash stage or flash stages;

(e) compensating the losses of water as a result of water present in the gas streams taken off at the top of the absorption stage and of the flash stage or flash stages by feeding in, at the bottom of the last flash stage or, where only one flash stage is used, at the bottom of this flash stage, an amount of steam substantially corresponding to the water loss and (f) recycling the regenerated absorption liquid to the absorption stage.

* * * * *